United States Patent

Crozafon

Patent Number: 5,609,630
Date of Patent: Mar. 11, 1997

[54] INTRAOCULAR IMPLANT

[76] Inventor: Philippe Crozafon, 55, Promenade des Anglais, 06000 Nice, France

[21] Appl. No.: 515,533

[22] Filed: Aug. 15, 1995

[30] Foreign Application Priority Data

Aug. 22, 1994 [FR] France .................. 94 10187

[51] Int. Cl.⁶ .............................................. A61F 2/16
[52] U.S. Cl. ................................................ 623/6
[58] Field of Search ..................................... 623/6

[56] References Cited

U.S. PATENT DOCUMENTS

| | | | |
|---|---|---|---|
| 4,412,359 | 11/1983 | Myers | 623/6 |
| 4,673,406 | 6/1987 | Schlegel | 623/6 |
| 5,078,742 | 1/1992 | Dahan | 623/6 |
| 5,180,390 | 1/1993 | Drews | 623/6 |

FOREIGN PATENT DOCUMENTS

| | | | |
|---|---|---|---|
| 0064770 | 11/1982 | European Pat. Off. . | |
| 0215468 | 3/1987 | European Pat. Off. . | |
| 0180887 | 5/1988 | European Pat. Off. . | |
| 0337390 | 10/1989 | European Pat. Off. . | |
| 0579528 | 1/1994 | European Pat. Off. . | |
| 2651117 | 3/1991 | France . | |
| 2681524 | 3/1993 | France . | |
| 2226246 | 6/1990 | United Kingdom | 623/6 |

*Primary Examiner*—Mary Beth Jones
*Attorney, Agent, or Firm*—Fisher, Christen & Sabol

[57] ABSTRACT

The present invention relates to an intraocular implant (1) which includes a central lens (2) and at least two elastically deformable securing arms (3), each of which is connected via one of its ends (4) to the central lens (2). Each of the securing arms (3) exhibits a general direction which is radial with respect to the central lens (2), and each of the securing arms includes, at its free end (6) opposite to the central lens (2), an arched bead (7) which is convex towards tho outside. The curvilinear length (L1) of the arched bead (7) is at least equal to a third of the diameter (D) of the central lens (2).

3 Claims, 2 Drawing Sheets

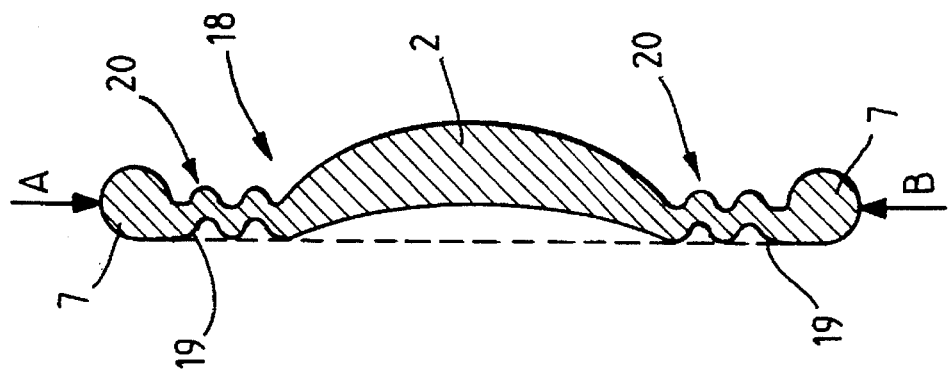
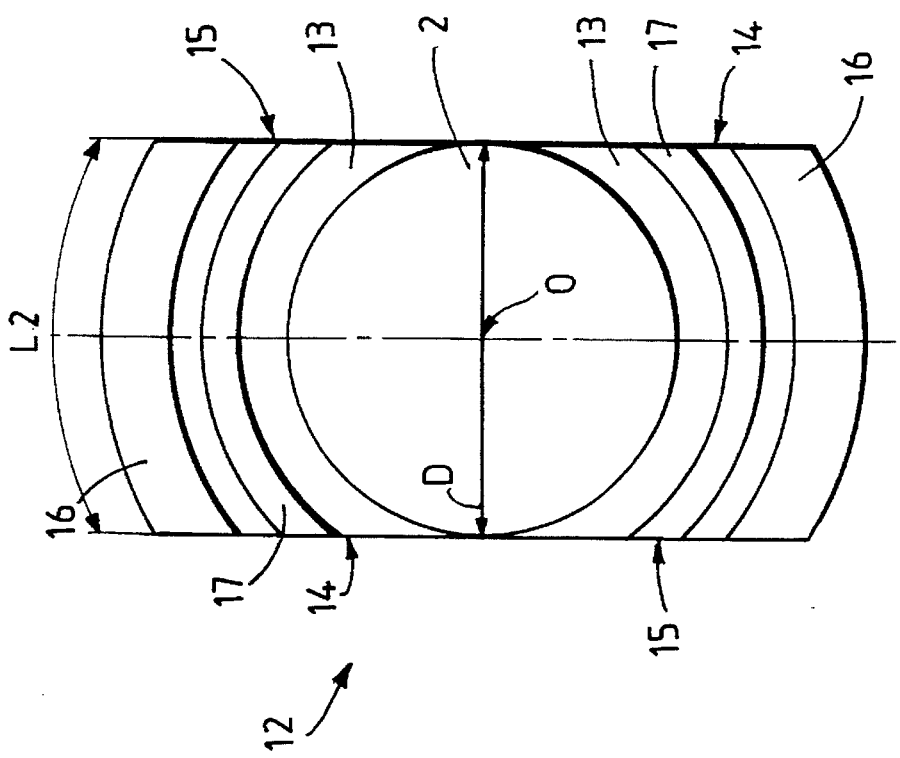

INTRAOCULAR IMPLANT

The present invention relates to an intraocular implant which is intended to be implanted, by surgical intervention, in the eyeball, and more specifically in the capsule of the eye.

Such an intraocular implant is more particularly suitable, although not exclusively so, for replacing the natural crystalline lens of the eye after a surgical intervention for cataract. It is known that cataract is distinguished by a partial or total opacity of the crystalline lens and often necessitates a surgical intervention which consists in performing an ablation of this crystalline lens which has become opaque, after incising the cornea and opening the capsule. Such an operation for cataract is generally accompanied by simultaneous or subsequent emplacement of an intraocular implant which is intended to replace the opaque crystalline lens which has just been ablated.

It is known that such an intraocular implant generally comprises, on the one hand, a central lens, and, on the other hand, securing means which are preferably made in the form of elastically deformable arms which are connected via one of their ends to the outer periphery of said central lens. These arms are intended for positioning and securing the intraocular implant in such a way as to render the latter integral with the eye.

However, as a result of poor securing by said arms, it can happen that said intraocular implant displaces laterally in such a way as to cause off-centering of the lens, which fact may prevent correct penetration of light rays into the eye and may cause, in particular, problems with vision.

Moreover, the emplacement of the intraocular implant, which constitutes work of great precision, requires an adapted shape of the lens and of the arms if it is to be performed easily, and this is especially the case when the incision in the cornea, through which the intraocular implant is introduced into the eyeball, is small.

Obviously, in a surgical intervention, the aim is to make the narrowest possible incision, among other reasons to alleviate any postoperative problems due to this incision.

Consequently, the shape and the physical properties, in particular the mechanical properties, of the arms are extremely important for achieving an easy emplacement and a reliable and durable securing of the intraocular implant.

It will be noted that the shape to be given to said arms depends essentially on the material from which the lens is made, and on the part of the eye in which said intraocular implant is to be implanted, on the one hand in order to adapt the arms to the shape of this part, and, on the other hand, on account of the stresses to which the intraocular implant is likely to be subjected there and which it is advisable to overcome.

Thus, for example, an intraocular implant placed in the capsule of a patient who has undergone an operation for cataract is subjected, in particular, to the effect of the cicatricial contractions of said capsule when the latter presents postoperative cicatricial fibrosis.

Such cicatricial contractions can generate a displacement of the intraocular implant in the capsule and can cause off-centering of the lens, and such off-centering can lead to imperfect focusing of images on the retina, which can create, in particular, visual aberrations such as diplopia, for example.

Consequently, in addition to permitting easy emplacement, one of the essential conditions to be fulfilled by such intraocular implants is that of guaranteeing good securing, and of doing this irrespective of the mechanical stresses to which said implants may be subjected.

The object of the present invention is to remedy the disadvantages mentioned hereinabove. It relates to an intraocular implant which can be implanted easily and which is capable of being secured, particularly in the capsule of the eye, in a reliable manner in such a way as to withstand any postoperative reactions, such as cicatricial fibrosis, for example.

To this end, according to the invention, the intraocular implant comprising a central lens, and at least two elastically deformable securing arms which are connected via one of their ends to said lens, is distinguished by the fact that each of said arms exhibits a general direction which is radial with respect to said lens, and by the fact that it comprises, at its free end opposite said lens, an arched bead convex toward the outside, the curvilinear length of said arched bead being at least equal to a third of the diameter of the lens.

Thus, said intraocular implant can be fixed in a very stable manner in said capsule of rounded shape, by way of said beads which, by virtue of their considerable length and their arched shape, allow for substantial contact with the internal wall of the capsule and prevent lateral displacement of the intraocular implant.

This securing is reinforced by the fact that the walls of the capsule, upon healing one over the other, envelop and hold said beads which are thus rendered integral with the capsule.

Moreover, on account of the arched shape of the beads, the intraocular implant can be introduced easily into the capsule by rotating the arms on the internal wall of said capsule.

In addition, by virtue of their general radial direction, said elastically deformable arms are capable of absorbing any postoperative stresses generated by the wall of the capsule, for example in the event of cicatricial fibrosis, in such a way as to protect the central lens.

The curvilinear length of said arched bead is preferably approximately equal to the diameter of the lens.

The arc of each of said beads is advantageously centered on the radial direction of the corresponding arm, which fact facilitates the resistance to mechanical stresses acting on the beads.

In addition, said arms advantageously have a width which is substantially constant and which is approximately equal to the length of the arc of the corresponding bead.

In order to facilitate the manipulation of the intraocular implant, a minimum number of wide arms necessary for the positioning, namely two arms, are provided on the central lens which is preferably of circular shape.

Moreover, these two arms are advantageously identical and are arranged in a symmetrical manner, in one plane, with respect to the center of said lens. This symmetrical and simplified shape of the intraocular implant also facilitates the manipulation and insertion of said intraocular implant.

Furthermore, said arms advantageously comprise at least one supplementary bead arranged between said central lens and said bead provided at the free end, this making it possible to reinforce the securing of the intraocular implant in the capsule, by the mode of attachment described previously, obtained by the walls of the capsule healing one over the other, thereby simultaneously and partially enclosing the arms equipped with beads.

Of course, within the scope of the present invention, said relatively wide arms can have different shapes.

The edges of said arms can advantageously have, in the plane of said lens, a curved shape or a rectilinear shape.

In addition, said arms advantageously have concentric undulations transverse with respect to the thickness of the arms and concentric with respect to the corresponding bead.

Said concentric undulations impart greater pliability to said arms, particularly in the direction of the stresses of the wall of the capsule in contact with said beads, which makes it possible to absorb any mechanical stresses of said capsule in such a way as to prevent off-centering of the lens which can be very prejudicial, as mentioned hereinabove.

Said central lens can obviously have different shapes within the scope of the present invention, and in particular a plano-convex shape.

However, the central lens is preferably made in the shape of a meniscus which is convex on the outer side of the intraocular implant and concave on the inner side.

Such a shape affords a two-fold advantage. On the one hand, said lens bends more easily than a lens having another shape, for example a biconvex shape, which fact facilitates the emplacement of the intraocular implant. On the other hand, the concave shape of the inner side makes it possible to reduce the capsular fibrosis on account of a reduced surface contact between the lens and the capsule.

From the figures in the attached drawing it will be clearly understood how the invention can be realized. In these figures, identical references denote similar elements.

FIG. 3 is a plan view of an intraocular implant formed in accordance with a second embodiment.

FIG. 4 is a longitudinal section, similar to the section in FIG. 2, of an intraocular implant formed in accordance with a third embodiment.

Figure 2:
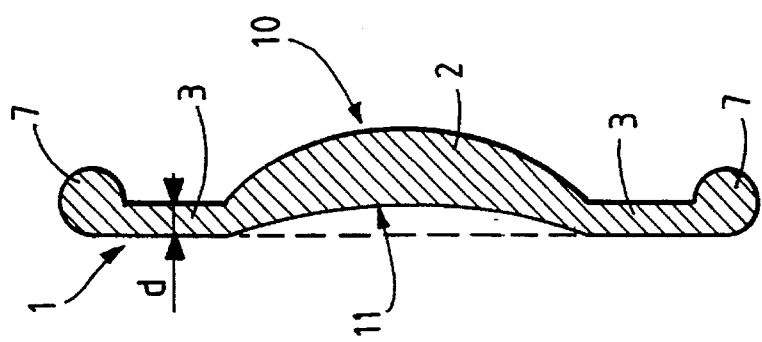
FIG. 2 is a longitudinal section of the intraocular implant along the line II—II in FIG. 1.
Figure 1:
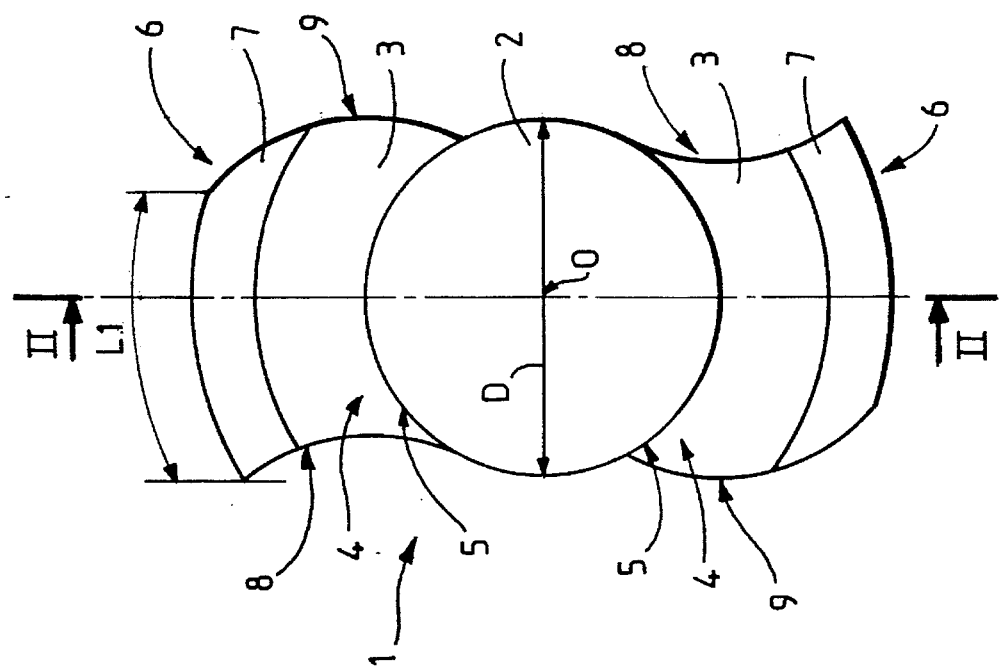
FIG. 1 is a plan view of an intraocular implant according to the invention.

The intraocular implant 1 according to the invention, as represented in FIGS. 1 and 2, can be used, for example, to replace the natural crystalline lens of the eye after an operation for cataract, said intraocular implant 1 being implanted for this purpose, for example, in the capsule of the eye (not shown).

Said intraocular implant 1, preferably made in one piece, either of polymethyl methacrylate, or of a special thermoplastic polymer, comprises a circular central lens 2, with center O and diameter D, and identical arms 3 which are elastically deformable and are connected via one 4 of their ends to the outer periphery 5 of said central lens 2 and are intended to position and secure said intraocular implant 1 in the capsule of the eye. Said arms 3 are symmetrical, in one plane, with respect to said center O of the lens 2. It will be noted, by way of example, that said intraocular implant can also be made of silicone or of acrylic.

According to the invention, each of said arms 3 has a general direction which is radial with respect to said lens 2, and comprises, at its free end 6 opposite said lens 2, an arched bead 7 convex toward the outside, the curvilinear length L1 of said arched bead 7 being at least equal to a third of the diameter D of the lens 2.

In the example shown, said curvilinear length L1 is approximately equal to the diameter D of the lens 2.

Moreover, the arc of each of said beads 7 is centered on the radial direction of the corresponding arm 3.

As can be seen in FIG. 2, said beads 7 project toward the outside of the intraocular implant 1, that part of the intraocular implant intended to be placed toward the outside of the eye being situated on the right in said FIG. 2.

Said beads 7 additionally have an approximately circular shape in cross section, although this shape is not exclusive, and other shapes can of course be envisaged within the scope of the present invention.

Furthermore, the arms 3 of thickness d have, on the one hand, edges 8 and 9 which are curved in a substantially identical manner, and, on the other hand, a width which is substantially constant and approximately equal to the length L1 of the arc of the beads 7, such as is shown in FIG. 1.

By virtue of the characteristics described hereinabove, the intraocular implant 1 according to the invention has in particular the following advantages:

the free end 6 of the arms 3 permits a substantial contact with the capsule in which the intraocular implant 1s to be implanted, on account of, on the one hand, the considerable curvilinear length L1, and, on the other hand, the arched shape of the beads 7 which is adapted to the rounded shape of said capsule;

said arched shape of the beads 7 furthermore permits easy surgical introduction of the implant 1 by rotation of said free end 6 on the internal wall of the capsule; and said beads 7 permit a strengthened attachment to the capsule by partial securing of the walls of said capsule on the intraocular implant.

After the intraocular implant has been placed in the capsule, the walls of said capsule in fact sag inward in such a way as to surround said beads and to come into contact with one another on the sides of the arms. Thus, by healing one over the other at the level of these parts which are in contact, said walls envelop the beads of the arms and render them integral with the capsule, which fact guarantees great stability of the intraocular implant 1.

Moreover, said arms 3 which are thus formed with a wide shape, and curved laterally, are capable of efficiently absorbing any postoperative stresses generated by the wall of the capsule, for example in the event of cicatricial fibrosis, in such a way as to protect the central lens 2, preventing in particular an off-centering of said lens.

In a preferred embodiment of the invention, the diameter D of the lens 2 and the curvilinear length L1 are approximately equal to 5.5 mm, the thickness d to 0.5 mm, and the diameter of the bead 7 in cross section is about 1 mm.

As can be seen in FIG. 2, said central lens 2 is made in the shape of a meniscus which is convex on the outer side 10 and concave on the inner side 11.

This concave shape of the inner side 11 makes it possible to reduce capsular fibrosis, on account of reduced surface contact between the lens 2 and the capsule on said inner side 11, in contrast to a plano-convex or biconvex shape which can also be envisaged for the lens 2.

Moreover, a lens 2 formed in this way bends much more easily, which fact obviously facilitates the emplacement of the intraocular implant 1.

In an alternative embodiment, such as is represented in FIG. 3, the intraocular implant 12 according to the invention comprises two identical arms 13 which are symmetrical with respect to the center O of the lens 2 and are formed in a rectilinear manner so that, on the one hand, their edges 14 and 15 are parallel to each other, said edges 14 and 15 being spaced apart from one another by a distance approximately equal to the diameter D of the central lens 2, and, on the other hand, the edge 14 of one of said arms 13 corresponds to the continuation of the edge 15 of the other arm 13, and vice versa.

In addition, each of said arms 13 is equipped not only with an end bead 16 of curvilinear length L2 similar to the bead 7 of the arm 3, but with a second bead which is disposed between the central lens 2 and said bead 16 in such a way as to present a shape which is similar and concentric to the shape of said end bead 16.

It is of course also possible to provide other supplementary beads on said arms 13.

Such an embodiment makes it possible to strengthen the securing of the intraocular implant 12 in the capsule, as a result of the walls of said capsule healing one over the other, as described hereinabove.

Indeed, by virtue of said supplementary beads 17, new anchoring elements are obtained for said walls of the capsule, making it possible to increase the stability with respect to said capsule.

In a second variant of the invention, such as is represented in FIG. 4, the intraocular implant comprises arms 19 which present, in section, a configuration with undulations 20, said undulations 20 being formed between the beads 7 disposed at the free end of the arms 19 and the central lens 2. For the rest, said intraocular implant 1 is identical to the intraocular implant 3, as can be seen by comparing FIGS. 2 and 4.

Said undulations 20 are concentric and present, in a front view (not shown), a rounded shape corresponding to the rounded shape of the beads 7.

By virtue of said concentric undulations 20, the arms 19 have a greater pliability, particularly in the directions indicated by arrows A and B and corresponding to the directions of possible stresses which may be exerted on the intraocular implant 18 by the wall of the capsule which is situated in contact with the beads 7 after implantation. This pliability thus allows said arms 19 to absorb such mechanical stresses of said capsule and thus prevent an off-centering of the central lens, such an off-centering being capable of provoking abnormalities of vision.

I claim:

1. An intraocular implant (1, 12, 18) having an outer side and an inner side, said intraocular implant comprising: a central lens (2) which is circular in shape, two elastically deformable securing arms (3, 13, 19) and beads (7, 16), each of said securing arms (3, 13, 19) having two ends and each of said securing arms (3, 13, 19) being connected via one of its ends to said central lens (2) and via the other of its ends to one of said beads (7, 16), said securing arms (3, 13, 19) having edges which have a shape curved in the plane of said central lens (2) and exhibiting a general direction which is radial with respect to said central lens (2), said securing arms (3, 13, 19) being identical to each other, said securing arms (3, 13, 19) having a substantially constant width which is approximately equal to the length of one of said beads, and said securing arms (3, 13, 19) being arranged in a symmetrical manner, in one plane, with respect to the center (O) of the central lens (2), and said beads (7, 16) being convex toward the outer side, the curvilinear length (L1, L2) of said bead (7, 16) being at least equal to a third of the diameter (D) of the central lens (2).

2. The intraocular implant as claimed in claim 1, wherein said securing arms (19) have concentric undulations (20) which are transverse with respect to the thickness of the securing arms (19) and concentric with the center (O) of said central lens (2).

3. The intraocular implant as claimed in claim 1, wherein the central lens (2) is made in the shape of a meniscus which is convex on the outer side (10) of the intraocular implant and concave of the inner side (11) of the intraocular implant.

* * * * *